United States Patent
Worrall

(10) Patent No.: US 6,841,168 B1
(45) Date of Patent: Jan. 11, 2005

(54) METHOD FOR THE PRESERVATION OF BIOLOGICALLY-ACTIVE MATERIAL

(75) Inventor: Eric Edward Worrall, Lampeter (GB)

(73) Assignee: Anhydro Limited, Scunthorpe (GB)

( * ) Notice: Subject to any disclaimer, the term of this patent is extended or adjusted under 35 U.S.C. 154(b) by 0 days.

(21) Appl. No.: 10/018,834

(22) PCT Filed: Jun. 21, 2000

(86) PCT No.: PCT/GB00/02254

§ 371 (c)(1),
(2), (4) Date: Dec. 19, 2001

(87) PCT Pub. No.: WO00/78924

PCT Pub. Date: Dec. 28, 2000

(30) Foreign Application Priority Data

Jun. 22, 1999 (GB) .............................. 9914412

(51) Int. Cl.⁷ .............................. A61K 9/10; A61K 9/14; A61K 31/00; A61K 31/70; A61K 38/00
(52) U.S. Cl. .................... 424/484; 424/488; 424/184.1; 514/1; 514/2; 514/44; 514/55; 435/260
(58) Field of Search ................................. 435/374, 200, 435/2, 236, 238, 243; 436/18; 514/55; 424/78.08, 189.1, 185.1, 192.1, 206.1, 290.1, 93.1, 94.1, 536, 484, 486, 489, 490, 496, 497, 85.2, 198.1, 278.1; 536/123.13

(56) References Cited

U.S. PATENT DOCUMENTS

| | | | | |
|---|---|---|---|---|
| 5,149,653 A | * | 9/1992 | Roser ......................... 435/260 |
| 5,654,008 A | * | 8/1997 | Herbert et al. .............. 424/489 |
| 5,672,301 A | * | 9/1997 | Orly et al. .................... 264/4.1 |
| 5,900,238 A | * | 5/1999 | Gombotz et al. ........ 424/184.1 |
| 5,972,707 A | * | 10/1999 | Roy et al. ................... 435/455 |
| 6,136,606 A | * | 10/2000 | Chatfield ................. 424/206.1 |
| 6,221,575 B1 | * | 4/2001 | Roser et al. .................... 435/2 |
| 6,391,318 B1 | * | 5/2002 | Illum et al. .............. 424/278.1 |

FOREIGN PATENT DOCUMENTS

| | | | |
|---|---|---|---|
| GB | WO 93/11220 | * | 6/1993 |
| GB | WO 96/40077 | * | 12/1996 |
| US | WO 99/27071 | * | 6/1999 |

OTHER PUBLICATIONS

Fernandez–Urrusuno et al., S.T.P. Pharma Sciences, vol. 9 No 5, PAges 429–436 (1999).*
Rweyemamu et al., "Contaious bovine pleuropneumonia vaccines: the need for improvements," Revue Scientifique et Technologique, Volumne 14(3), 593–601 (1995)—MEDLINE abstract.*
Kiarie et al., Clinical and Diagnostic Laboratory Immunology, vol. 3(6), pp. 746–752 (1996).*

* cited by examiner

*Primary Examiner*—James Housel
*Assistant Examiner*—Zachariah Lucas
(74) *Attorney, Agent, or Firm*—Bret E. Field; Bozicevic, Field & Francis LLP

(57) ABSTRACT

Biologically-active material can be preserved by a method of desiccation, without lyophilisation, in a matrix of glassy trehalose. The method involves forming a coacervate of the biologically-active material and chitosan and then dehydrating mixture of coacervate and trehalose solution. In a cycle time much shorter than a typical freeze drying process biologically-active material, such as viruses, proteins and nucleic acids, can be preserved to provide a material that can be rehydrated. The invention is especially useful for the production of vaccines from preserved material.

48 Claims, No Drawings

METHOD FOR THE PRESERVATION OF BIOLOGICALLY-ACTIVE MATERIAL

The present invention relates to the preservation of biologically-active material, e.g. viruses, bacteria and biomolecules. In particular, it relates to an ultra-rapid method by which such material can be preserved using chitosan and the disaccharide trehalose. By this method a long term preservation of biomolecules and microorganisms can be achieved and, especially, living attenuated vaccines can be prepared.

The preservation of biodegradable materials by dehydration and osmoconcentration is a familiar and ancient technology. When the task of preserving sensitive biomolecules became necessary, simple drying by dehydration failed, as structural water was removed, causing subsequent denaturation and loss of vital activity. Cryopreservation in liquid nitrogen and lyophilisation have become the accepted methods for the long term preservation of sensitive biomolecules, the latter method being used extensively for the preservation of live attenuated vaccines.

Improved thermotolerance of freeze dried Rinderpest vaccine has been achieved by extending the secondary drying cycle, in order to reduce residual moisture (RM) levels to around 1%–2%. This entails long and high energy consuming operational cycles of up to 72 hours as described by Mariner, J. C. et al., Vet. Microbiol., 1990, 21, 195–209. Vaccines produced by this method are known and are distinguished from the standard vaccine by the name "THERMOVAX".

As mentioned above, these currently used processes are time consuming and involve high energy input Furthermore, lyophilisation confers only a modest level of thermotolerance in the final product and refrigeration is still required to reduce deterioration during storage. This is a particular problem for live vaccines to be used in tropical climates since these lose potency with the unfortunate result that vaccination programs carried out in the field in tropical countries, where monitoring the "cold chain" is difficult, can ultimately lead to the vaccination of patients with substandard or, in some cases, useless vaccine. During evolutionary natural selection, certain species of plants and animals acquired the remarkable and elegant ability to tolerate extreme dehydration, remaining dormant in hostile environments for very long periods of time and yet able to assume complete vital activity on rehydration. Examples include the resurrection plant *Selaginella lepidophyla*, the brine shrimp *Artemia salina* (Clegg, J., J. Comp. Biochem. Physiol, 1967, 20, 801–809), the yeast *Saccharomyces cerevisiae* (Coutinho, E., Journal of Biotechnology, 1988, 7, 23–32) and the tardigrade *Macrobiotus hufelandi*(Kinchin, I. M., Biologist, 1995, 42, 4). Such organisms are termed cryptobiotic and the process by which they survive is known as anhydrobiosis. All species of animals and plants which display this ability contain the disaccharide trehalose (α-D-glucopyranosyl-α-D-glucopyranoside). Its presence, generally in the order of 0.2 g/g dry cell weight in most cryptobionts, enables them to resist extreme dehydration, high temperatures, X-rays and also, in some species of tardigrades, pressures as high as 600 MPa.

Colaco et al., Biotechnology, 1992, 10, 1007–1011, describe the benefit of rapid drying of biological materials using trehalose. This method mostly refers to the drying of restriction enzymes and immunoglobulins onto preformed solid matrices, such as cellulose fibres or onto the surfaces of plastic plates for diagnostic purposes such as ELISA or similar diagnostic applications in the laboratory. Problems arise, however, with these techniques when scaling up to industrial applications, such as large scale commercial vaccine production where much larger unit numbers and volumes have to be handled using mandatory aseptic techniques in partially sealed vials. To meet the operational requirements of large scale vaccine production, where unit volumes from 1.0 ml upwards and production batches of 20 liters are typical, a different strategy is required to remove the volume of water in an economically acceptable time. Drying at atmospheric pressure even at the highest physiologically tolerated temperatures would require an unacceptably long time to remove water quickly enough from partially stoppered vaccine vials and would inevitably result in denaturation and loss of potency. Nishimura. K. et al, VACCINE 3 No. 5 (1985) show that chitosan coacervates have a high affinity for mucosal epithelia. It was suggested that this might intensify the active transport of antigen into the cells, thus stimulating both IgA and IgG systemic immune response.

The present invention is primarily concerned with a method of preserving biologically-active material using chitosan and trehalose under conditions which cause water to be removed while, at the same time, allowing the biological integrity of the material to be maintained.

Accordingly, the invention provides a method of preserving biologically-active material which comprises mixing an aqueous suspension of the biologically-active material with a sterile aqueous solution of chitosan or non-toxic salt thereof to form a coacervate of the biologically-active material and chitosan or non-toxic salt thereof, adding to the coacervate a sterile aqueous solution of trehalose, subjecting the sterile aqueous mixture of coacervate and trehalose to drying at a pressure of less than atmospheric and at a temperature, initially no greater than 37° C., which is controlled not to fall to 0° C. or below to form a glassy porous matrix comprising metastable glassy trehalose containing, within the matrix, chitosan or non-toxic salt thereof and desiccated biologically-active material.

According to a preferred embodiment, the method of preserving a biologically-active material comprises the steps:

(i) mixing an aqueous suspension of the biologically-active material with a sterile aqueous solution of chitosan or a non-toxic salt thereof to form a coacervate of the biologically-active material and chitosan or non-toxic salt thereof;

(ii) mixing with the coacervate produced in step (i) a sterile aqueous solution of trehalose;

(iii) subjecting the mixture to primary drying, for 30 to 60 minutes, at a pressure of less than atmospheric and at a temperature initially no below and which finally is no greater than 40° C., to form a glassy porous matrix comprising glassy trehalose having a residual moisture content of not greater then 10% and containing, within the matrix, chitosan or non-toxic salt thereof and desiccated biologically-active material; and (iv) subjecting the glassy porous matrix of step (iii) to secondary drying for 10 to 30 hours at a pressure not greater than 0.1 mbar and at a temperature which finally is in the range of from 40 to 45° C. to form a trehalose matrix having a residual moisture content of not greater than 2% containing, within the matrix, chitosan or non-toxic salt thereof and desiccated biologically-active material.

By using the method of the invention it is possible to produce a live vaccine with, compared to prior art methods, enhanced biological characteristics and distinct commercial advantages. Vaccines prepared using the method of the invention are dried much more quickly than those using conventional freeze drying procedures. For instance, the method of the invention can be used to prepare trehalose/chitosan/biologically-active material mixtures to a moisture content of about 10% in less than one hour. Further dehydration to a residual moisture content of about 1–2% can be achieved in less than 30 hours, for instance about 20 hours compared to a period of 50 hours by conventional freeze drying procedures. Furthermore, damage caused by solute concentration is minimised according to the present invention and particularly damaging ice crystallisation is avoided. The thermostability of the biologically-active material preserved in the trehalose glassy matrix is greater than that of materials preserved by prior art methods and, thus, the necessity of the "cold chain", which is a serious constraint with conventional freeze-dried vaccine, is minimised. The product of the present invention can be exposed to high ambient temperatures, e.g., up to about 45° C., for prolonged periods without serious loss of biological activity. In addition to these, and other advantages, of the present invention the product of the method exhibits instantaneous "flash solubility" upon rehydration.

The method of the present invention is suitable for achieving the long term preservation of biologically-active materials, for example, microorganisms, proteins, living biomolecules and nucleic acids. In particular, it can be used to preserve highly labile live attenuated viral components and mycoplasma components that can be rehydrated to form vaccines. Examples of such biologically-active materials that can be preserved according to the method of the invention include:

Family: Paramyxoviridiae
Subfamily: Paramyxovirinae
Genera: Parainfluenza virus group, Measles, Rinderpest, canine distemper, Peste des Petits Ruminants (PPR)
*Paramyxovirus*: mumps virus (Mumps)
Genus: *Rubivirus*, Rubella (German Measles)
Genus: *Flavivirus*, Yellow fever virus (Yellow Fever)
Genus: *Rhabdoviruses*, Lyssaviridiae (Rabies virus)
Picoma viruses (Polio virus)
Newcastle Disease virus
*Mycoplasma: Mycoplasma mycoides* (Contagious Bovine Pleuropneumonia)

*Brucella abortus*: Strain 19 vaccine.

According to the method of the present invention, the biologically-active material to be preserved is prepared as a suspension in an appropriate aqueous medium. It may be the case that a virus or bacterial strain will need to be cultured, for instance in vero cells, in an appropriate culture medium, and then harvested prior to suspension in order to provide a useful concentration of material. Typically, the aqueous suspension of biologically active material will be pH adjusted, for example by the addition of an alkali, to a pH in the range of from 7.0 to 7.8 especially about 7.4.

The suspension of biologically-active material will then be mixed with a sterile aqueous solution of chitosan or a non-toxic salt thereof. Chitosan is the general name given to a class of cationic polysaccharides prepared by the deacetylation of chitin, (poly N-acetyl glucosamine) to (poly,1,4-beta-D-glucopyranosamine). Chitin is a natural biopolymer which occurs abundantly in the exoskeletons of crustaceans. The cuticles of tardigrades in the highly resistant "tun" state are composed of chitin. Chitosan is a linear cationic polyelectrolyte which is non-toxic, biodegradable and biocompatible and is a white or off-white amorphous translucent solid which is soluble in dilute organic acids. The use of chitosan in the present invention is based on the discovery that it acts as a protective biopolymer shell around the biologically-active material being preserved. Thus, the use of chitosan in combination with the controlled method of desiccation described herein improves the thermal tolerance of the desiccated material. Typically, the concentration of the chitosan in the sterile aqueous solution used for admixture with the suspension of biologically-active material will be in the range of from 0.001% to 0.02% w/v. Excellent results have been obtained using a solution containing 0.01% w/v chitosan. The chitosan is preferably used in the form of a non-toxic acid addition salt, e.g., chitosan HCl, which is more soluble than chitosan.

The chitosan solution and the suspension of biologically-active material are typically mixed in a volume ratio of about 1:1, at a pH of 7.4, at a temperature of from above 0° C. to 37° C., preferably less than 20° C. and most preferably about 4° C. The chitosan and the biologically-active material are preferably subjected to vigorous agitation, e.g., by vortex stirring for up to 60 seconds at a temperature in the range of from 2 to 6° C., preferably about 4° C. to produce a homogeneous mixture. The mixture will, typically, be allowed to stand while maintaining the temperature to allow a coacervate, i.e. an absorption complex of the chitosan and the biologically-active material wherein the biologically-active material becomes coated with the chitosan, to form. The thus-formed coacervate is then collected, typically by centrifugation. This chitosan coacervate precipitation is useful for concentrating low titre vaccine pools and/or for reducing process volumes for drying. Preferably, the centrifugation step is carried out not more than one hour after mixing the chitosan solution and the suspension of biologically-active material. If the mixture is stored for a longer period the particles of coacervate precipitate, rather than being light and homogeneous, tend to clump together. The centrifugation is preferably conducted in a refrigerated centrifuge, typically maintained at about 4° C., at a typical speed of about 10,000 rpm for several minutes. Following collection, the coacervate is preferably resuspended in an appropriate medium, e.g. Hanks balanced salt solution (HBSS) or Hanks lactalbumin yeast extract (Hanks LYE) before being mixed with a sterile solution of trehalose. The coacervate will, in general, be resuspended in a volume of appropriate medium which is equal to the volume of the liquid prior to centrifugation so that the concentration of biologically-active material in the coacervate suspension is the same as it was in the liquid prior to centrifugation. However, the biologically-active material can be concentrated, if desired, by resuspending the coacervate into a volume of appropriate medium which is smaller than the volume of the liquid prior to centrifugation. By concentrating the biologically-active material in this way the volume of water that needs to be removed during the vacuum drying stage is effectively reduced, thus reducing the amount of energy required during evaporative drying and reducing the period of time required to dry the material in accordance with the method of the invention. In the case where the biologically-active material is a virus it may often be beneficial to concentrate the virus, i.e., to increase the titre of the virus, in this way.

Trehalose is one of the most stable and chemically non-reactive disaccharides. It has an extremely low bond energy of less than 1 Kcal/Mol making the dimer structure very stable. It does not undergo caramelisation unless heated severely, nor does it cause the Maillard reaction with proteins or peptides. The natural di-hydrate structure containing two water molecules enables unusual flexibility around the disaccharide bond which possibly permits a closer association with tertiary structured biomolecules. It is not hygroscopic yet exhibits "flash solubility" on hydration, a property particularly useful for dried vaccines.

The sterile aqueous solution of trehalose used in the method of the present invention will typically have a trehalose concentration of from 0.20% to 10% w/v, although it is possible to use solutions having a higher concentration (e.g., 50% w/v) of trehalose to provide the final required concentration of trehalose in the mixture which is subjected to drying. Preferably, the trehalose concentration will be 2 to 10% and more preferably 2.5 to 8% w/v. Within the range of trehalose concentrations, the actual concentration used will, in general, depend on the unit size of the biologically-active material. Less trehalose is required for small virus particles than for large cells.

The mixture of the sterile aqueous solution of trehalose and resuspended coacervate, when prepared, is subjected to vacuum drying. Preferably a conventional freeze drying apparatus (e.g., such as manufactured by EDWARDS, CHRIST, USIFROID or SAVANT) is used for the drying procedure in order to provide a controlled environment for the critical stages in the method. It is emphasised, however, that if such an apparatus is used freeze drying conditions are not employed and the material is not subjected freeze drying. The initial temperature of the drying apparatus is such as to ensure that the trehalose/coacervate mixture will not be greater than 37° C. and will preferably be 37° C. in order to prevent any loss of biological activity at this stage in the method. As water is evaporated off the mixture, the temperature of the mixture falls. The desiccation is, however, carried out to ensure that no freezing or sublimation from ice occurs as is normally experienced in conventional freeze drying procedures, i.e. the temperature of the product during this stage of the drying process is controlled not to fall to 0° C. or below and is typically controlled not to fall below 4° C. The pressure is reduced below atmospheric pressure, preferably to a value of from 800 to 300 mbar.

The drying stage is continued for a period of time, typically between 30 and 60 minutes, during which time the temperature of the trehalose/coacervate mixture initially falls as water is evaporated off and then rises. When a temperature (under the reduced pressure employed) of about 25° C. is reached the trehalose forms a glassy matrix. The moisture content of the glassy matrix is about 10%. The temperature of the material at the end of this drying procedure should preferably be controlled so that it does not exceed 40° C. since the biologically-active material will sustain damage if the temperature is allowed to rise above this.

It is preferred that the method of the invention utilizes a drying procedure that comprises two drying stages, a primary drying stage (as described above) in which the residual moisture content of the material is reduced to a value of not greater than 10% and a secondary drying stage in which the residual moisture content of the material is reduced further to a value not exceeding 2%. The secondary drying stage, if used, is carried out following a primary drying stage as described above preferably without removal of the material from the drying apparatus used for the primary drying stage. In a secondary drying stage the glassy matrix obtained at the end of the primary drying stage is further dehydrated under a reduced pressure not exceeding 0.1 mbar. Currently-available specialised apparatus has the ability to operate at extremely low pressures, for instance below 0.001 mbar. However, very good results have been obtained according to the present invention using reduced pressures for the secondary drying stage in the range of from 0.001 to 0.1 mbar, typically from 0.01 to 0.1 mbar. The secondary drying stage is continued for a total period of time in the range of from 10 to 30 hours, preferably 20 to 30 hours.

As mentioned above, the temperature of the glassy matrix at the end of the primary drying stage should not exceed 40° C. During the secondary drying stage the temperature of the matrix may rise slightly to a final temperature, at the end of the drying procedure, of from 40° C. to 45° C. The trehalose matrix, at the end of the secondary drying stage will have a residual moisture content of 2% or less, preferably 1% or less, in order to ensure a very high degree of thermostability in the product. At such residual moisture contents the final temperature in the drying process should not be higher than 45° C. since the desiccated biologically-active material in the matrix may undergo some degree of destruction above 45° C. Preferably, the temperature of the product at the end of the secondary drying stage will not exceed 44° C.

It has been found, through experimentation that there is some benefit in controlling the temperature of the matrix, during the secondary drying stage, such that it is maintained at about 37° C. for a period of from 15 to 17 hours and then raising this gradually (for instance by 0.5 to 1° C. per hour), over the remaining secondary drying time to a final temperature within the range of 40° C. to 45° C.

The glassy trehalose matrix produced according to the method can be stored for long periods of time, e.g. several weeks, without any substantial loss of vital activity and without the need for refrigeration and can be rehydrated very quickly in an appropriate aqueous medium, typically sterile distilled water, to produce a vaccine for use in a very short period of time.

The preparation of a vaccine and the operating procedure using a freeze dryer for the desiccation of biologically-active material such as the viruses Rinderpest and Peste des Petits Ruminants viruses, and mycoplasma without a lyophilisation step involving sublimination from ice, exploits the unique property of the disaccharide trehalose to protect tertiary macromolecules during desiccation.

Compared to conventional freeze-drying procedures the method of the invention offers the following benefits:

- It provides a high level of protection for the biologically-active material, employing a relatively short, simple procedure. An even higher level of protection is provided by using the preferred two stage drying procedure which may use a 25 hour cycle.
- Production cycle time and energy costs are, thus, reduced compared to typical freeze drying procedures.
- Basic drying equipment is all that is required, although sophisticated microprocessor controlled freeze dryers can also be used, but are not strictly essential.
- The method is tolerant of power interruption, unlike lyophilisation where even a short power failure can cause product melting, leading to unacceptable loss of virus.

Oral vaccination with some attenuated strains of virus has in the past been difficult to achieve because of the loss of epitheliotropism. Both oral and intranasal vaccination would be useful and appropriate for many applications because they mimic the natural route of droplet infection, generating a cascade of protective mucosal immunity, with IgA and humoral IgG2a T helper-cell type 1 response. It would be easy to administer such routes of vaccination and these would be applicable in the event that a suitable vaccine is prepared. Chitosan increases the transcellular and paracellular transport across mucosal epithelium and is thought to enhance or restore diminished epitheliotropism commonly associated with attenuated vaccine strains (e.g., attenuated RBOK Rinderpest virus and CBPP S1/44 mycoplasma). This may be particularly important in CBPP and other mycoplasma infections where the protective mechanisms are still obscure, particularly post vaccination immunity following subcutaneous vaccination. A vaccination procedure with live attenuated strains mimicking the natural route of infection induces a more comprehensive sero mucous and cell mediated immunity. According to a further aspect the present invention provides a method of making a vaccine for oral or intranasal use which comprises preparing a glassy matrix of trehalose containing desiccated virus according to the above described method and rehydrating the glassy matrix with an appropriate aqueous composition. According to a preferred embodiment of this aspect of the invention the vaccine for oral or intranasal vaccination is an MMR vaccine. Since the current paediatric MMR vaccine is prepared by conventional freeze drying technology and is injected into the patient subcutaneously, an oral or intranasal vaccine would give great benefits.

EXAMPLE 1

Method for the Preparation of a Bivalent Live Attenuated Veterinary Vaccine

Rinderpest virus RBOK strain was grown in vero cells in Hanks LYE (lactalbumin hydrolysate and yeast extract) medium containing 0.1% trehalose instead of glucose. Contagious Bovine Pleuropneumonia (CBPP) *Mycoplasma mycoides* subs. *mycoides* S1/44 (SC) $T_r$-SR was grown in Gourlay medium. The virus pool and the CBPP pool were then harvested. The pH of the virus and the CBPP pool were adjusted with 0.1M NaOH to pH 7.4.

A stock 2% w/v solution of chitosan was prepared as follows:

| | |
|---|---|
| Chitosan HCl (supplied by Pronova Seacure) | 20 g |
| Distilled water | 1000 ml |

Autoclaved at 121° C. for 30 minutes.

A stock solution of 50% w/v trehalose dihydrate in Hanks Balanced Salt Solution (HBSS) was prepared the pH being adjusted by the addition of 0.1M NaOH to 7.4. The solution was sterilised by autoclaving at 121° C. for 20 minutes.

A suitable volume of working strength 0.02% w/v chitosan was prepared by adding 1 ml of stock 2% w/v chitosan to 99 ml of sterile distilled water.

One volume of 0.02% w/v chitosan solution was added to one volume of virus fluid at 4° C. and the pH adjusted to 7.4 with 0.1M NaOH. This step was repeated separately for the CBPP culture pool and the resulting coacervation complex of each was completed by rapid vortex stirring for 30 seconds and subsequently stored at 4° C. for 1 hour. The resulting precipitate of each was collected by centrifugation at 10,000 rpm in a refrigerated centrifuge, the supernatant discarded and the coacervate resuspended in one volume of Hanks balanced salt solution (HBSS). A volume of sterile 50% w/v solution of trehalose in Hanks balanced salt solution (HBSS) was added to the coacervate suspension give a final trehalose concentration of 5% w/v (potency is checked by the quality control standard operating procedures for these organisms).

The vaccine was dried by filling 11.0 ml aliquots into 5 ml vaccine vials partially stoppered with dry butyl rubber stoppers. The shelves of the conventional freeze dryer (EDWARDS MODULYO) were heated to 37° C. and the condenser was allowed to reach minus 40° C. The vaccine vials were placed in the dryer and the pressure in the drying chamber was adjusted to 800 mbar and drying commenced for 30 minutes until approximately 75% of the water had evaporated, taking care not to allow the product temperature to fall below 0° C. The pressure was then lowered to 500 mbar and drying was continued until the glass transition temperature of trehalose was reached at approximately 25° C., a glassy porous matrix was formed, and the temperature of the product was allowed to rise to reach the initial starting temperature close to that of the shelves. At this stage the residual moisture (RM) was approximately 10%. Further drying at 0.01 mbar and 45° C. for 17 hours reduced this to 1–2% RM ensuring high thermostability in the product.

The pressure was maintained at 0.01 mbar and the vials were sealed under vacuum or at atmospheric pressure under dry nitrogen.

Results

The effectiveness of the present invention was demonstrated by measuring the titres of Rinderpest virus and the CBPP mycoplasma in their respective parent liquids and then in vaccines prepared from the dehydrated product obtained according to the Example above.

Rinderpest Virus

1. Virus titre of parent liquid before drying 5.40 Log 10 TCID 50/ml.
2. Virus titre in product of the Example (dried with 2.5% trehalose) 5.45 Log 10 TCID 50/ml.
   where TCID 50/ml=tissue culture infective dose 50 per ml.

CBPP mycoplasma

1. Titre of live mycoplasma parent liquid before drying 9.90 Log 10 orgs/ml.
2. Titre of product of the Example (after drying with 5% trehalose) 8.05 Log 10 orgs/ml

EXAMPLE 2

Materials and Methods

Preparation of a PPR Vaccine Culture

Peste des petits ruminants (PPRV 75/1) strain was grown initially using vero cells in Glasgow medication Eagles medium (GMEM) supplemented with 10% tryptose phosphate broth (TPB, Difco) and 10% foetal calf serum (FCS) as follows:

Vero cells were seeded into 5×1 50 cm$^2$ plastic flasks at a cell concentration of 287,000 cells/ml, 60 ml per flask. Two flasks were inoculated with 0.5 ml PPR virus suspension at a multiplicity of infection of 0.03 virus particles/cell. One flask remained uninoculated as a control.

The flasks were incubated at 37° C. in 5% $CO_2$ and cells examined daily for development of cytopathic effects (cpe). On day 4 the GMEM medium was replaced with Hanks lactalbumin yeast extract (Hanks LYE), containing 2% FCS and 0.1% trehalose dihydrate. On day 6 the cpe was approximately 80% and the virus harvests were pooled, frozen and stored at −20° C. The control flask remained in the incubator for 10 days, and proved to be free from contamination or cell degradation, with no obvious sign of adventitious agents.

Chitosan Solution

A stock 2% w/v aqueous solution of chitosan (Seacure Cl 310) was prepared in distilled water and sterilized in an autoclave at a temperature of 121° C. for 30 minutes. The stock solution was diluted using sterile distilled water to give a solution containing 0.02% w/v chitosan.

Method

The pH of the virus fluid was adjusted to 7.4 using 0.1 M NaoH. To one part of the pH adjusted virus fluid was added one part of the 0.02% w/v diluted chitosan solution and the mixture was vortex stirred for 30 seconds. The stirred mixture was allowed to rest for 1 hour at 4° C. to allow complete formation of the coacervate complex.

Immediately, at the end of the one hour rest period, the coacervate mixture was centrifuged at 10,000 rpm in a refrigerated centrifuge for 20 minutes. The resulting supernatant was discarded and the precipitated complex was collected and suspended in Hanks LYH medium +2% FBS at a pH 7.4. The total volume of the resuspension medium was equal to the total volume of the liquid as submitted to centrifugation.

One part of the resuspended complex was mixed with one part of a sterile 5% w/v aqueous solution of trehalose dihydrate, thus giving a fluid trehalose concentration of 2.5% w/v trehalose in the mixture.

One ml volumes were distributed into each of 5 ml vaccine vials and partially sealed with dry vented butyl rubber inserts. This application was carried out at room temperature, in a laminar air flow biohazard cabinet and observing strict aseptic precautions.

Primary Drying

The dehydration process was carried out using an Edwards Supermodulyo freeze dryer with precise control over chamber pressure, condenser pressure, shelf and product temperatures. The freeze dryer was prepared in advance before loading the shelf chamber with the vials containing the product The shelf temperature was raised to 40° C. and the condenser temperature was allowed to reach the operational limit of 40° C. Vials were then placed on the shelves and the contents allowed to reach 35° C. The chamber door was closed with the macro and micro air admittance valves fully opened and the vacuum pump switched on with full gas ballast. The pressure in the chamber was adjusted to 800 mbar by carefully closing the macro air admittance valve. The pressure in the condenser was maintained at 500 mbar in order to produce a pressure gradient between the chamber and condenser and this provided the driving force to induce water vapour to flow from the product surface to the condenser. Partial closure of the vials with the stoppers also had the beneficial effect of throttling the aperture thus increasing the pressure still further at the product surface. It was noticed that the partially closed vials dried quicker than the fully open ones containing the temperature recording thermocouples.

The product temperature was controlled primarily by carefully closing the macro air admittance valve during the first 15 minutes, and thereafter by manipulation of the micro air admittance valve, making sure not to allow the product to freeze. Maintaining a temperature around 1–2° C. caused by evaporative cooling, increased the evaporation rate so that 90% of the water had evaporated within one hour and the product temperature began to rise to match the shelf temperature. As dehydration proceeded a critical point was reached after 40 minutes when there was a sudden rapid rise to 25° C. followed within seconds by a sudden fall in product temperature to 15° C. This was accompanied by a dramatic bubbling of the product.

Secondary Drying

The batch was then subjected to a period of secondary drying where the temperature was raised over a period of a further 17 hours to a final product temperature of 42.4° C. and a pressure of 0.06 mbar, with gas ballast fully closed. This had the effect of reducing the residual moisture content of the material to approximately 0.72%.

What is claimed is:

1. A method of preserving biologically-active material comprising mixing an aqueous suspension of the biologically-active material with a sterile aqueous solution of chitosan or a non-toxic salt thereof to form a coacervate of the biologically-active material and chitosan or non-toxic salt thereof, adding to the coacervate a sterile aqueous solution of trehalose, subjecting the sterile mixture of coacervate and trehalose to drying at a pressure less than atmospheric and at a temperature which is initially less than or equal to 37° C. and thereafter may fall provided that the temperature does not fall to, or below, 0° C. to form a glassy porous matrix comprising metastable glassy trehalose containing, within the matrix, desiccated biologically-active material and chitosan or non-toxic salt thereof.

2. A method according to claim 1, wherein the biologically-active material is selected from viruses, bacteria, tertiary structured biologically-active protein and nucleic acid.

3. A method according to claim 2, wherein the biologically-active material is at least one virus selected from Rinderpest Virus, Peste de Petit Ruminants Virus, Measles, Mumps, Rubella, Yellow Fever, Polio, and Newcastle Disease Virus.

4. A method according to claim 2, wherein the biologically-active material is *Mycoplasma mycoides*.

5. A method according to any one of claims 1 to 4, wherein the sterile aqueous solution of chitosan or non-toxic salt thereof has a chitosan concentration of 0.01% w/v.

6. A method according to claim 5, wherein the sterile aqueous chitosan solution and the aqueous suspension of biologically-active material are mixed at a volume ratio of 1:1 at pH 7.4.

7. A method according to claim 1, wherein the coacervate of biologically-active material and chitosan is subjected to vortex mixing.

8. A method according to claim 1, wherein the coacervate of biologically-active material and chitosan is mixed with a sterile aqueous trehalose solution having a trehalose concentration in the range of from 0.20 to 20% w/v.

9. A method according to claim 8, wherein the sterile aqueous solution of trehalose has a trehalose concentration in the range of from 2.6 to 8% w/v.

10. A method according to claim 9, wherein the sterile aqueous solution of trehalose has a trehalose concentration of about 5% w/v.

11. A method according to claim 1, wherein the drying stage is carried out at a pressure of not greater than 800 mbar.

12. A method according to claim 1, wherein the resulting trehalose matrix containing desiccated biologically-active material and chitosan or non-toxic salt thereof. Is subjected to a secondary drying procedure for 10 to 30 hours at a pressure not greater than 0.1 mbar and at a temperature which is in the range of from 40 to 45° C. to form a trehalose matrix having a residual moisture content of not greater than 2% containing, within the matrix, desiccated biologically-active material and chitosan or non-toxic salt thereof.

13. A method according to claim 12, wherein secondary drying is carried out for 20 to 30 hours.

14. A method according to claim 12, wherein secondary drying is carried out for 16 to 17 hours at a temperature of about 37° C. and the temperature is, thereafter, raised gradually over the remaining secondary drying time to a final temperature in the range of from 40 to 45° C.

15. A method according to claim 12, wherein the residual moisture content at the end of the secondary drying step is 1.0% or lower.

16. A method of making a vaccine comprising preserving a biologically-active material according to the method of claim 1 and rehydrating the glassy product obtained thereby in an appropriate aqueous medium.

17. A method according to claim 16, wherein the vaccine is for oral or intranasal use.

18. A method according to claim 16, wherein the vaccine is a Measles, Mumps, Rubella (MMR) vaccine.

19. A rehydratable composition comprising trehalose in the form of a metastable glass matrix containing, within the matrix, a coacervate of a desiccated biologically-active material and chitosan or a non-toxic salt thereof.

20. A rehydratable composition according to claim 19 which has a residual moisture content of not greater than 2%.

21. A rehydratable composition according to claim 20 which has a residual moisture content of not greater than 1%.

22. A rehydratable composition according to claim 19, useful on rehydration for making a vaccine.

23. A rehydratable composition according to claim 19, wherein the biologically-active material is selected from viruses, bacteria, tertiary structured biologically-active proteins and nucleic acids.

24. A rehydratable composition according to claim 23, wherein the biologically-active material is at least one virus selected from Rinderpest Virus, Peste de Petit Ruminants Virus, Measles, Mumps, Rubella, Yellow Fever, Polio, and Newcastle Disease Virus.

25. A rehydratable composition according to claim 23, wherein the biologically-active material is *Mycoplasma mycoides*.

26. A method of preserving biologically-active material comprising mixing an aqueous suspension of the biologically-active material with a sterile aqueous solution of chitosan or a non-toxic salt thereof to form a coacervate of the biologically-active material and chitosan or non-toxic salt thereof, adding to the coacervate a sterile aqueous solution of trehalose, subjecting the sterile mixture of coacervate and trehalose to drying for a period of 30 to 60 minutes at a pressure less than atmospheric and at a temperature, which is initially less than or equal to 37° C. and thereafter may fall provided that the temperature does not fall to, or below 0° C. and wherein the final temperature is less than or equal to 40° C. to form a glassy porous matrix comprising metastable glassy trehalose having a residual moisture content of less than or equal to 10% containing, within the matrix, desiccated biologically-active material and chitosan or non-toxic salt thereof.

27. A method according to claim 26, wherein the biologically-active material is selected from viruses, bacteria, tertiary structured biologically-active protein, and nucleic acid.

28. A method according to claim 27, wherein the biologically-active material is at least one virus selected from Rinderpest Virus, Peste de Petit Ruminants Virus, Measles, Mumps, Rubella, Yellow Fever, Polo, and Newcastle Disease Virus.

29. A method according to claim 27, wherein the biologically-active material is *Mycoplasma mycoides*.

30. A method according to claim 26, wherein the sterile aqueous solution of chitosan or non-toxic salt thereof has a chitosan concentration of 0.01% w/v.

31. A method according to claim 30, wherein the sterile aqueous chitosan solution and the aqueous suspension of biologically-active material are mixed at a volume ratio of 1:1 at pH 7.4.

32. A method according to claim 26, wherein the coacervate of biologically-active material and chitosan is subjected to vortex mixing.

33. A method according to claim 26, wherein the coacervate of biologically-active material and chitosan is mixed with a sterile aqueous trehalose solution having a trehalose concentration in the range of from 0.20 to 20% w/v.

34. A method according to claim 33, wherein the sterile aqueous solution of trehalose has a trehalose concentration in the range of from 2.5 to 8% w/v.

35. A method according to claim 26, wherein the drying stage is carried out at a pressure of not greater than 800 mbar.

36. A method of preserving biologically-active material comprising mixing an aqueous suspension of the biologically-active material with a sterile aqueous solution of chitosan or a non-toxic salt thereof to form a coacervate of the biologically-active material and chitosan or non-toxic salt thereof, adding to the coacervate a sterile aqueous solution of trehalose, subjecting the sterile mixture of coacervate and trehalose to drying for a period of from 30 to 60 minutes at a pressure not greater than 800 mbar and at a temperature which is initially less than or equal to 37° C. and thereafter may fall provided that the temperature does not fall to, or below, 0° C. to form a glassy porous matrix comprising metastable glassy trehalose having a residual moisture content of less than or equal to 10% containing, within the matrix, desiccated biologically-active material and chitosan or non-toxic salt thereof, and then subjecting the resulting trehalose matrix containing desiccated biologically-active material and chitosan or non-toxic salt thereof to a secondary drying procedure for 10 to 30 hours at a pressure not greater than 0.1 mbar and at a temperature which is in the range of from 40 to 45° C. to form a trehalose matrix having a residual moisture content of not greater than 2% containing, within the matrix, desiccated biologically-active material and chitosan or non-toxic salt thereof.

37. A method according to claim 36, wherein the biologically-active material is selected from viruses, bacteria, tertiary structured biologically-active protein, and nucleic acid.

38. A method according to claim 37, wherein the biologically-active material is at least one virus selected from Rinderpest Virus, Peste de Petit Ruminants Virus, Measles, Mumps, Rubella, Yellow Fever, Polio, and Newcastle Disease Virus.

39. A method according to claim 37, wherein the biologically-active material is *Mycoplasma mycoides*.

40. A method according to claim 36, wherein the coacervate of biologically-active material and chitosan is mixed with a sterile aqueous trehalose solution having a trehalose concentration in the range of from 0.20 to 20% w/v.

41. A method according to claim 40, wherein the sterile aqueous solution of trehalose has a trehalose concentration in the range of from 2.5 to 8% w/v.

42. A method according to claim 36, wherein secondary drying 19 carried out for 20 to 30 hours.

43. A method according to claim 36, wherein secondary drying is carried out for 15 to 17 hours at a temperature of about 37° C. and the temperature is, thereafter, raised gradually over the remaining secondary drying time to a final temperature in the range of from 40 to 45° C.

44. A method according to claim 36, wherein the residual moisture content at the end of the secondary drying step is 1.0% or lower.

45. A method of making a vaccine comprising preserving a biologically-active material according to the method of claim 26 and rehydrating the glassy product obtained thereby in an appropriate aqueous medium.

46. A method of making a vaccine comprising preserving a biologically-active material according to the method of claim 36 and rehydrating the glassy product obtained thereby in an appropriate aqueous medium.

47. A method according to claim 46, wherein the vaccine is for oral or intranasal use.

48. A method according to claim 46, wherein the vaccine is a Measles, Mumps, Rubella (MMR) vaccine.

* * * * *